(12) United States Patent
Sato

(10) Patent No.: US 6,506,376 B2
(45) Date of Patent: Jan. 14, 2003

(54) LIQUID MAKEUP COSMETIC

(75) Inventor: Hiroshi Sato, Fujioka (JP)

(73) Assignee: Mitsubishi Pencil Kabushiki Kaisha (JP)

(*) Notice: Subject to any disclaimer, the term of this patent is extended or adjusted under 35 U.S.C. 154(b) by 0 days.

(21) Appl. No.: 09/902,591

(22) Filed: Jul. 12, 2001

(65) Prior Publication Data

US 2002/0037304 A1 Mar. 28, 2002

(30) Foreign Application Priority Data

Jul. 27, 2000 (JP) ........................................ 2000-227426

(51) Int. Cl.$^7$ .......................... A61K 31/74; A61K 7/04; A61K 6/00; A61K 7/00; A61K 9/14
(52) U.S. Cl. .................... 424/78.03; 424/401; 424/489; 424/61
(58) Field of Search ................. 424/401, 489, 424/78.03, 61

(56) References Cited

U.S. PATENT DOCUMENTS 5,478,552 A * 12/1995 Hasegawa .................... 424/63
2002/0031534 A1 * 3/2002 Horino ....................... 424/401

FOREIGN PATENT DOCUMENTS

| JP | 7-196449 | 8/1995 | |
| JP | 2700816 | 10/1997 | |
| JP | 2704730 | 10/1997 | |
| JP | 2741237 | * 1/1998 | ............ A61K/7/02 |

* cited by examiner

Primary Examiner—Thurman K. Page
Assistant Examiner—Humera N. Sheikh
(74) Attorney, Agent, or Firm—Burns, Doane, Swecker & Mathis, L.L.P.

(57) ABSTRACT

A liquid makeup cosmetic comprising the following components (a), (b) and (c):

| (a) an acryl-silicone base graft copolymer, | 3 to 20% by weight |
| (b) a spherical fine particle powder, and | 5 to 30% by weight |
| (c) a low boiling silicone oil | 10 to 70% by weight, | and a liquid makeup cosmetic applicator which uses a brush as an applying means and which is charged therein with the liquid makeup cosmetic described above. Used are a mixed solution of an acryl silicone-base graft copolymer and decamethylcyclopentanesiloxane as the acryl-silicone base graft copolymer, an organic spherical powder of nylon, etc. or an inorganic spherical powder of magnesium silicate, etc. as the spherical fine particle powder and low polymerization degree dimethylpolysiloxane, etc. as the low boiling silicone.

2 Claims, No Drawings

LIQUID MAKEUP COSMETIC

BACKGROUND OF THE INVENTION

1. Field of the Invention

The present invention relates to a liquid makeup cosmetic and a cosmetic applicator charged therein with the cosmetic.

2. Description of the Related Art

Makeup put on with a liquid cosmetic such as a foundation, an eye liner and an eye shadow has so far been liable to cause blurring and wrinkling of a cosmetic film brought about by sweat, tear and sebum and degradation such as peeling with touch, and a synthetic resin emulsion and an oil-soluble resin which have film-forming ability have been used for the above cosmetics as a countermeasure therefor.

Japanese Patent No. 2704730 provides a cosmetic which forms a film that is excellent in water resistance, oil resistance and physical properties by blending a specific acryl-silicone base graft copolymer as a film-forming agent and which has high makeup functionality and high utility.

Japanese Patent No. 2741237 provides a non-aqueous makeup cosmetic which is excellent in water resistance, oil resistance and abrasion resistance and which is improved in a makeup function, characterized by comprising 5.0 to 30.0% by weight of an acryl-silicone base graft copolymer, 2.5 to 30.0% by weight of a low viscosity silicone oil, 20.0 to 80.0% by weight of a volatile hydrocarbon oil and 10.0 to 50.0% by weight of a cosmetic powder.

Japanese Patent No. 2700816 relates to a solid gel composition comprising an acryl-silicone base copolymer and a silicone oil having a viscosity of 50 mPa·s or less and a cosmetic comprising the same and provides a cosmetic which has the smooth and fresh touch and stability with the passage of time, and which is easy to use and is excellent in feeling in use.

Japanese Patent No. Hei 7-196449 provides a eye-makeup cosmetic which forms a homogeneous film and has good spreading, good water resistance and sebum resistance, particularly which has high strength and a good adhesive property of the film and therefore is excellent in makeup durability, feeling in use and stability with the passage of time, characterized by comprising trimethylsiloxysilicic acid, an acryl-silicone base graft copolymer, a low boiling silicone oil and/or low boiling isoparaffin base hydrocarbon.

However, a synthetic resin emulsion and an oil-soluble resin which have so far been used as a film-forming agent have not necessarily been satisfactory as a countermeasure for blurring and wrinkling of a cosmetic film brought about by sweat, tear and sebum and makeup degradation such as peeling with tough. Also, use of an acryl-silicone base graft copolymer has improved blurring, wrinkling and makeup degradation, but it has not been satisfactory in terms of a extendering property and feeling in use.

An object of the present invention is to provide a liquid makeup cosmetic which is excellent in water resistance, sebum resistance, an effect for preventing makeup degradation and makeup durability and which has a good extendering property and clean feeling in use in makeup.

SUMMARY OF THE INVENTION

Intensive researches repeated by the present inventors have resulted in finding that a liquid makeup cosmetic which solves the subject described above can be obtained by using a specific acryl-silicone base graft copolymer as a film-forming agent in combination with a low boiling silicone oil and a spherical fine particle powder as a lubricant, and thus the present invention has come to be completed.

That is, the present invention relates to a liquid makeup cosmetic comprising the following components (a), (b) and (c):

| | |
|---|---|
| (a) an acryl-silicone base graft copolymer, | 3 to 20% by weight |
| (b) a spherical fine particle powder, and | 5 to 30% by weight |
| (c) a low boiling silicone oil | 10 to 70% by weight |

Preferably, the makeup cosmetic described above is charged into a liquid cosmetic applicator equipped with a brush used as an applying means.

The liquid cosmetic of the present invention has excellent dipersibility and a good adhesive property to a skin, and in addition thereto, it is rich in water resistance and sebum resistance and has excellent effects on preventing blurring and wrinkling of a cosmetic film, makeup degradation and makeup fading. Further, obtained is a cosmetic which has excellent makeup durability and can uniformly be extended without causing unevenness and which has smooth and fresh feeling in use.

DETAILED DESCRIPTION OF THE PREFERED EMBODIMENTS

The acryl-silicone base graft copolymer of the component (a) used in the cosmetic of the present invention is a known substance described in Japanese Patent No. 2704730 and can be synthesized by radically copolymerizing a dimethylpolysiloxane compound having a radically polymerizable group at one end of a molecular chain with a radically polymerizable monomer comprising principally acrylate and/or methacrylate.

In this case, the dimethylpolysiloxane compound having a radically polymerizable group at one end of a molecular chain, which is a raw material, includes a compound represented by the following formula (I):

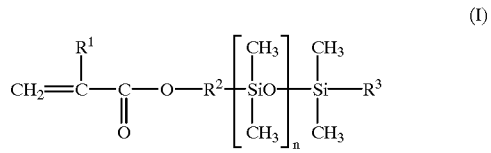

(I)

wherein $R^1$ represents a methyl group or a hydrogen atom; $R^2$ represents a divalent saturated hydrocarbon group having 1 to 10 carbon atoms and a linear or branched carbon chain which is intercalated with one or two ether bonds; $R^3$ represents a methyl group or a butyl group; and n represents a number of 3 to 300.

The radically polymerizable monomer comprising principally acrylate and/or methacrylate, which is other raw material, is a compound having one radically polymerizable unsaturated bond in a molecule, and given as the acrylate and/or methacrylate used in this case are alkyl (meth) acrylate such as methyl (meth)acrylate, ethyl (meth)acrylate, n-butyl (meth)acrylate and 2-ethylhexyl (meth)acrylate, hydroxyalkyl (meth)acrylate such as 2-hydroxyethyl (meth) acrylate and 2-hydroxypropyl (meth)acrylate, stearyl (meth) acrylate, behenyl (meth)acrylate and perfluoroalkyl (meth) acrylate having a fluorocarbon chain having 1 to 10 carbon atoms.

Commercially available products can be used as the acryl-silicone base graft copolymer and include, for example, KP-545 (manufactured by Shin-etsu Chemical Co., Ltd.) which is a mixed solution of an acryl-silicone base graft copolymer and decamethylcyclopentanesiloxane.

A blending amount of the acryl-silicone base graft copolymer described above is preferably 3 to 20% by weight based on the whole cosmetic. It is blended more preferably in a range of 5 to 15% by weight. If it is used in this range, the expected water resistance and sebum resistance can be secured, and makeup can be accomplished without causing blurring and wrinkling.

In the cosmetic of the present invention, the spherical fine particle powder used as the component (b) includes, for example, organic spherical powders of nylon, polyacrylonitrile, polyester, polypropylene, polyethylene, polystyrene, silicone and cellulose and inorganic spherical powders of magnesium silicate, calcium silicate and silicic acid anhydride. The spherical fine particle powder has preferably an average particle diameter of 0.05 to 100 μm, more preferably 0.05 to 20 μm.

Preferred commercial products of the spherical fine particle powder include, for example, P-1500 (manufactured by Catalysts & Chemicals Ind. Co., Ltd.), PS-500 (manufactured by Toray Industries, Inc.) and Tospearl (manufactured by GE Toshiba Silicone, Ind. Co., Ltd.).

At least one of the spherical fine particle powders can be selected, if necessary, and a surface thereof may be subjected to treatment such as oil treatment, silicone treatment, fluorine compound treatment, surfactant treatment, amino acid base compound treatment and water-soluble high polymer treatment. A blending amount of the spherical fine particle powder described above falls preferably in a range of 5 to 30% by weight, more preferably 10 to 20% by weight based on the whole cosmetic.

In the cosmetic of the present invention, the low boiling silicone oil used as the component (c) includes chain and cyclic silicone oils, for example, low polymerization degree dimethylpolysiloxane, octamethylcyclotetrasiloxane and decamethylcyclopentanesiloxane. Commercial products thereof include, for example, KF994 and KF995 (manufactured by Shin-etsu Chemical Co., Ltd.).

The low boiling silicone oils described above can be used alone or in suitable combination of optional two or more kinds thereof. A blending amount of the low boiling silicone oil falls preferably in a range of 10 to 70% by weight, more preferably 30 to 50% by weight based on the whole amount of the cosmetic. These low boiling silicone oils not only has action as a dissolving agent for the acryl-silicone base graft copolymer described above but also is an important element for elevating more the durability of the adhesive property and strength of the makeup film.

Further, a water-based component, an oil-based component and a powder component which are used for conventional cosmetics, in addition to the essential components described above, may be compounded in the cosmetic of the present invention. To be specific, capable of being compounded as long as the effects of the present invention are not damaged are, for example, a humidifier, a preservative, an antioxidant, a UV absorber, a beauty component, a perfume, a water-soluble high polymer, an extender pigment, a coloring pigment, an organic powder, a hydrophobicity-treated pigment and a synthetic organic food additive.

The cosmetic of the present invention obtained in the manner described above can be prepared in the form of a liquid makeup cosmetic compounded with a powder regardless of the uses thereof, and capable of being prepared therefrom are, for example, cosmetics such as foundations, eye liners, eye shadows, rouges, lipsticks and mascaras. The liquid makeup cosmetic of the present invention is most suitably applied a, liquid cosmetic applicator of a pen type which uses a brush as an applying means, and it is used particularly preferably in the form in which it is charged into such an applicator.

The reason why the liquid makeup cosmetic of the present invention has excellent characteristics which have not so far been obtained is that effectively exhibited are both of makeup durability brought about by the acryl-silicone base graft copolymer and easiness in use attributable to the spherical fine particle powder, and it is confirmed that if the components (a) to (c) are used in a range of a specific combination, that is:

| | |
|---|---|
| (a) acryl-silicone base graft copolymer, | 3 to 20% by weight |
| (b) spherical fine particle powder, and | 5 to 30% by weight |
| (c) low boiling silicone oil | 10 to 70% by weight | the expected extendering property and fresh feeling in use can be obtained as shall be shown in working examples described later. Such characteristics can be achieved principally by addition of the spherical fine particle powder and a blending balance between the respective components.

EXAMPLES

Next, the present invention shall be explained in further details with reference to examples and comparative examples, but the present invention shall by no means be restricted by these examples.

Examples 1 and 2 and Comparative Examples 1 to 4

Eye shadows according to recipes shown in Table 1 were prepared to carry out tests and sensory evaluation of water resistance, sebum resistance, makeup durability, a extendering property and fresh feeling in use by the following methods. The results thereof are shown together in Table 1.

Water resistance:

A suitable amount of the sample was put on a glass plate to form a coating film having a fixed film thickness by means of an applicator. After drying, the film was rubbed with a finger in water to evaluate a state thereof.

Sebum resistance:

A suitable amount of the sample was put on a glass plate to form a coating film having a fixed film thickness by means of an applicator. After drying, artificial sebum was coated thereon by means of the applicator, and after fixed time passed, the film was rubbed with a finger to evaluate a state thereof. Makeup durability, extendering property and fresh feeling in use:

The sample was subjected to an actual use test and evaluated.

TABLE 1

|  | Examples | | Comparative Examples | | | |
| --- | --- | --- | --- | --- | --- | --- |
| Components | 1 | 2 | 1 | 2 | 3 | 4 |
| Acryl-silicone base graft copolymer*[4] | 8.00 | 8.00 | 8.00 | 8.00 | 2.00 | 21.00 |
| Spherical silica (spherical fine particle powder)*[1] | 15.00 | — | — | — | — | — |
| Nylon powder (spherical fine particle powder)*[2] | — | 15.00 | — | 31.00 | 15.00 | 15.00 |
| Mica | — | — | 15.00 | — | — | — |
| Decamethylcyclopentanesiloxane*[3] | 45.00 | 45.00 | 45.00 | 29.00 | 51.00 | 32.00 |
| Silicon dioxide | 5.40 | 5.40 | 5.40 | 5.40 | 5.40 | 5.40 |
| Sucrose fatty acid ester | 3.00 | 3.00 | 3.00 | 3.00 | 3.00 | 3.00 |
| 1,3-Butylene glycol | 2.00 | 2.00 | 2.00 | 2.00 | 2.00 | 2.00 |
| Ethyl paraoxybenzoate | 0.05 | 0.05 | 0.05 | 0.05 | 0.05 | 0.05 |
| Propyl paraoxybenzoate | 0.05 | 0.05 | 0.05 | 0.05 | 0.05 | 0.05 |
| Methyl paraoxybenzoate | 0.10 | 0.10 | 0.10 | 0.10 | 0.10 | 0.10 |
| Butyl paraoxybenzoate | 0.10 | 0.10 | 0.10 | 0.10 | 0.10 | 0.10 |
| Diisostearyl malate | 2.00 | 2.00 | 2.00 | 2.00 | 2.00 | 2.00 |
| Di-2-ethylhexaneneopentyl glycol | 1.80 | 1.80 | 1.80 | 1.80 | 1.80 | 1.80 |
| Trimethylsiloxysilicic acid | 0.30 | 0.30 | 0.30 | 0.30 | 0.30 | 0.30 |
| Mica titan | 6.00 | 6.00 | 6.00 | 6.00 | 6.00 | 6.00 |
| Red iron oxide-coated mica | 10.00 | 10.00 | 10.00 | 10.00 | 10.00 | 10.00 |
| Yellow iron oxide-coated mica titan | 1.20 | 1.20 | 1.20 | 1.20 | 1.20 | 1.20 |
| Total | 100.00 | 100.00 | 100.00 | 100.00 | 100.00 | 100.00 |
| Test items | | | | | | |
| Water resistance | ⊚ | ⊚ | ⊚ | Δ | X | ⊚ |
| Sebum resistance | ⊚ | ⊚ | ⊚ | Δ | X | ⊚ |
| Makeup durability | ⊚ | ⊚ | ⊚ | Δ | X | ⊚ |
| Extending property | ○ | ⊚ | Δ | ⊚ | ⊚ | Δ |
| Fresh feeling in use | ⊚ | ⊚ | X | ⊚ | ⊚ | Δ |

*[1] P-1500 (Catalysts & Chemicals Ind. Co., Ltd.)
*[2] PS-500 (Toray Industries Inc.)
*[3] KF 995 (Shin-Etsu Chemical. Co., Ltd.)
*[4] KP 545 (Shin-Etsu Chemical Co., Ltd.)

<Evaluation criteria>
⊚: very good
○: good
Δ: a little good
X: inferior

What is claimed is:

1. A liquid makeup cosmetic comprising the following components (a), (b) and (c):
   (a) an acryl-silicone base graft 3 to 20% by weight copolymer,
   (b) A spherical fine particle 5 to 30% by weight power, said fine particle being used as a lubricant and having an average diameter of 0.05 to 100 μm,
   (c) a low boiling silicone oil more than 30 by weight and less than or equal to 50% by weight.

2. A liquid makeup cosmetic applicator which uses a brush as an applying means and which is charged therein with the liquid makeup cosmetic as claimed in claim 1.

* * * * *

UNITED STATES PATENT AND TRADEMARK OFFICE
CERTIFICATE OF CORRECTION

PATENT NO.   : 6,506,376 B2
DATED        : January 14, 2003
INVENTOR(S)  : Hiroshi Sato It is certified that error appears in the above-identified patent and that said Letters Patent is hereby corrected as shown below:

<u>Column 5,</u>
Line 45, before "spherical" change "A" to -- a --; change "power" to -- powder --.

Signed and Sealed this

Ninth Day of September, 2003

JAMES E. ROGAN
*Director of the United States Patent and Trademark Office*